(12) United States Patent
Danishefsky et al.

(10) Patent No.: US 6,548,661 B1
(45) Date of Patent: Apr. 15, 2003

(54) METHOD FOR THE MODIFICATION OF ALCOHOLS ON POLYMER SUPPORTS

(75) Inventors: Samuel J. Danishefsky, Englewood, NJ (US); Kenneth A. Savin, Indianapolis, IN (US); Jonathan C. G. Woo, New York, NY (US)

(73) Assignee: Sloan Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 09/160,373

(22) Filed: Sep. 24, 1998

Related U.S. Application Data
(60) Provisional application No. 60/060,029, filed on Sep. 25, 1997.

(51) Int. Cl.$^7$ ............................. C07H 1/00; C07H 3/06
(52) U.S. Cl. ....................... 536/124; 536/123; 536/18.6; 525/342
(58) Field of Search ................................ 536/123, 124, 536/18.6; 525/342

(56) References Cited

U.S. PATENT DOCUMENTS 5,625,030 A * 4/1997 Williams et al. ............. 528/361

OTHER PUBLICATIONS

Randolf, J. et al "Major simplification in oligosaccharide syntheses arising from a solid phase based method . . . " (1995) J. Am. Chem. Soc. vol. 117, pp. 5712–5719.*

Boehm, T. et al. "Development of a novel silyl ether linker for solid–phase organic synthesis" (1996) J. Org. Chem. vol. 61, pp. 6498–6499.*

Seeberger et al., "Synthesis of Biologically Important Oligosaccharides and Other Glycoconjugates by the Glycal Assembly Method", Aldrichimica Acta, vol. 30(3): 75–92, 1997.*

Danishefsky et al., "Glycals in Organic Synthesis: The Evolution of Comprehensive Strategies for the Assembly of Oligosaccharides and Glycoconjugates of Biological Consequence", Angew. Chem. Int. Ed. Engl. vol. 35: 1380–1419, 1996.*

Commissions on Nomenclature of Organic Chemistry and Physical Organic Chemistry, IUPAC, Pure and Applied Chemistry, vol. 67: 1325 and 1334, 1995.*

Collins and Ferrier. Monosaccharides: Their Chemistry and Their Roles in Natural Products, publ. by John Wlley & Sons, Ltd., p. 4, 1995.*

Chan, T.–H., et al., Polymer–anchored Organosilyl Protecting Group in Organic Synthesis, J. Chem. Soc., Chem. Commun., 909–911 (1985).

Randolph, J. T., et al., "Major Simplifications in Oligosaccharide Syntheses Arising from a Solid–Phase Based Method: An Application to the Synthesis of the Lewis b Antigen," J. Amer. Chem. Soc., 117, 5712–5719 (1995).

Roberge, J. Y. et al., "A Strategy for a Convergent Synthesis of N–Linked Glycopeptides on a Solid Support," Science (Washington, D. C. ), 269, 202–204 (1995).

* cited by examiner

Primary Examiner—James O. Wilson
Assistant Examiner—Leigh C. Maier
(74) Attorney, Agent, or Firm—Choate, Hall & Stewart; Brenda Herschbach Jarrell; Nadege M. Lagneau (57) ABSTRACT

The present invention provides a polymer-linked composition having the structure:

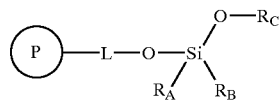

wherein $R_A$ and $R_B$ are each independently a linear or branched chain alkyl or an aryl group; wherein Ⓟ is a polymeric support; wherein L is a linker selected from the group consisting of a single bond; a saturated or unsaturated oligomethylene chain, etc., a 1,4-phenylene; or a 1,4-phenylenemethylene moiety, said moiety being optionally substituted by at least one linear or branched alkyl, alkoxy group etc.; and wherein $R_C$ is a linear or branched acyclic, cyclic or multicyclic moiety, said moiety being optionally unsaturated and/or substituted by at least one hydrogen, $OR^i$, alkyl, etc.; wherein $R^i$ is hydrogen, CHO, $COOR^{ii}$, or a substituted or unsubstituted linear or branched chain alkyl, etc.; wherein if $R_C$ is cyclic, said moiety is optionally aromatic and/or heterocyclic; or if multicyclic, said moiety is optionally a fused multicyclic, fully or partially aromatic and/or heterocyclic. Methods are provided for preparing and cleaving such compositions, which are useful in the preparation of glycopeptides and other glycoconjugates.

27 Claims, 4 Drawing Sheets

METHOD FOR THE MODIFICATION OF ALCOHOLS ON POLYMER SUPPORTS

This application is based on U.S. Provisional Application Serial No. 60/060,029, filed Sep. 25, 1997, the contents of which are hereby incorporated by reference into this application.

This invention was made with government support under grant AI-16943-19 from the National Institutes of Health. Accordingly, the U.S. Government has certain rights in the invention.

FIELD OF THE INVENTION

This invention is in the field of solid-phase organic synthesis, and specifically relates to a method of linking complex and sterically demanding hydroxylic compounds to a solid support for subsequent synthetic transformation and polymer-linked compositions obtained thereby. The method is especially suited to the preparation of complex carbohydrates and glycoconjugates such as glycopeptides.

BACKGROUND OF THE INVENTION

New methods of preparing complex glycoconjugates are needed in view of the growing recognition of the role played by complex carbohydrates as signaling molecules in the context of biological processes has recently gained prominence. M. L. Phillips, et al., *Science*, 1990, 250, 1130; M. J. Polley, et al., *Proc. Natl. Acad. Sci. USA*, 1991 88, 6224: T. Taki, et al., *J. Biol. Chem.*, 1996, 261, 3075). For example, the carbohydrate domains of the blood group substances contained in both glycoproteins and glycolipids are distributed in erythrocytes, epithelial cells and various secretions. Such determinants are encountered as markers for the onset of various tumors. K. O. Lloyd, *Am. J. Clinical Path.*, 1987, 87, 129; K. O. Lloyd, *Cancer Biol.*, 1991, 2, 421. Carbohydrate-based tumor antigenic factors have applications at the diagnostic level, as resources in drug delivery or ideally in immunotherapy. Toyokuni, T., et al., *J. Am. Chem Soc.* 1994, 116, 395; Dranoff, G., et al., *Proc. Natl. Acad. Sci. USA* 1993, 90, 3539; Tao, M-H.; Levy, R., *Nature* 1993, 362, 755; Boon, T., *Int. J. Cancer* 1993, 54, 177; Livingston, P. O., *Curr. Opin. Immunol.* 1992, 4, 624; Hakomori, S., *Annu. Rev. Immunol.* 1984, 2, 103; K. Shigeta, et al., *J. Biol. Chem.* 1987, 262, 1358.

Antigens which are selective (or ideally specific) for cancer cells could prove useful in fostering active immunity. Hakomori, S., *Cancer Res.*, 1985, 45, 2405–2414; Feizi, T., *Cancer Surveys* 1985, 4, 245–269. Novel carbohydrate patterns are often presented by transformed cells as either cell surface glycoproteins or as membrane-anchored glycolipids. In principle, well chosen synthetic glycoconjugates which stimulate antibody production could confer active immunity against cancers which present equivalent structure types on their cell surfaces. Dennis, J., *Oxford Clycostems Glyconews*, Second Ed., 1992; Lloyd, K. O., in *Specific Immunotherapy of Cancer with Vaccines*, 1993, New York Academy of Sciences, pp.50–58. Chances for successful therapy improve with increasing restriction of the antigen to the target cell. For example, one such specific antigen is the glycosphingolipid isolated by Hakomori and collaborators from the breast cancer cell line MCF-7 and immunocharacterized by monoclonal antibody MBr1. Bremer, E. G., et al., *J. Biol. Chem.* 1984, 259, 14773–14777; Menard, S., et al., *Cancer Res.* 1983, 43, 1295–1300.

An improved strategy for linking carbohydrates to solid supports would facilitate glycopeptide synthesis. Such a strategy would aid in the assembly of complex glycoconjugates, which require a high degree of convergence and relief from the burdens associated with the manipulation of blocking groups. An improved linking method would also allow greater flexibility in the conjugation of the carbohydrate determinant with carrier proteins or lipids. Bernstein, M. A.; Hall, L. D., *Carbohydr. Res.* 1980, 78, Cl; Lemieux, R. U., *Chem. Soc. Rev.* 1978, 7, 423; R. U. Lemieux, et al., *J. Am. Chem. Soc.* 1975, 97, 4076. This is a critical condition if the synthetically derived carbohydrates are to be incorporated into carriers suitable for biological application.

Accordingly, the subject invention provides a novel approach to the synthesis of complex carbohydrates on polymer supports. In particular, the invention provides a new and generally applicable substrate-linking procedure for use in a wide variety of systems, including not only glycoconjugates but other complex organic systems containing at least one hydroxyl group. Roberge, J. Y. et al., *Science*, 1995, 269, 202; Randolph, J. T. et al., *J. Am. Chem. Soc.* 1995, 117, 5712; Danishefsky, S. J. et al., *Science*, 1993, 260, 1307. Prior solid state methods of glycopeptide synthesis suffer from the limitation that the initial silylation event which serves to "load" the polymer provides poor coupling efficiencies when the loading is conducted at positions which bear relatively hindered glycoxyl centers.

The present methods have generated glycoconjugates not available by prior art methods. Huang, W-Q. *J. Chem. Soc., Chem. Commun.* 1985, 909. In the present method, even sterically encumbered alcohols can be attached to a solid support with little or no prior manipulation of a commercially available polymer, e.g., hydroxymethyl-polystyrene. The process requires only inexpensive materials and the linker is compatible with a variety of reaction conditions. Furthermore, the present method is applicable in an automatic glycal-based carbohydrate synthesizer, as the linker can be cleaved quickly without damaging the original polymer support (FIG. 1(b)). As a result, the solid support is then immediately ready for reloading, thereby providing an important economic advantage over prior methods.

SUMMARY OF THE INVENTION

One object of the present invention is to provide a method of linking complex hydroxylic compounds to a solid polymeric support. Specifically, the method disclosed herein uses a silylene linker to attach a hydroxylic compound to the support.

A particular object of the invention is to provide a polymer-linked composition having the structure:

wherein $R_A$ and $R_B$ are each independently a $C_{1-6}$ linear or $C_{3-10}$ branched chain alkyl or an aryl group; wherein Ⓟ is a polymeric support; wherein L is a linker selected from the group consisting of a single bond; a saturated or unsaturated oligomethylene chain, said oligomethylene chain being optionally interrupted by oxygen or sulfur atoms, an alkyl- or arylamino moiety, NH—CO or CO—NH; a 1,4- phenylene; or a 1,4-phenylenemethylene moiety, said moiety being optionally substituted by at least one linear or branched alkyl or alkoxy group and/or halogen atom; and wherein $R_C$ is a linear or branched acyclic, cyclic or multicyclic moiety, said moiety being optionally unsaturated and/or substituted by at least one hydrogen, $OR^i$, amino, alkyl- or dialkylamino, $NHCOR^i$, halogen, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein $R^i$ is hydrogen, CHO, $COOR^{ii}$, or a substituted or unsubstituted linear or branched chain alkyl, arylalkyl or aryl group aryl, alkylaryl or arylalkyl; wherein if $R_C$ is cyclic, said moiety is optionally aromatic and/or heterocyclic; or if multicyclic, said moiety is optionally a fused multicyclic, fully or partially aromatic and/or heterocyclic.

A further object of the invention is to provide a method for preparing a polymer-linked composition having the structure:

wherein $R_A$ and $R_B$ are each independently a $C_{1-6}$ linear or $C_{3-10}$ branched chain alkyl or an aryl group; wherein Ⓟ is a polymeric support; wherein L is a linker selected from the group consisting of a single bond; a saturated or unsaturated oligomethylene chain, said oligomethylene chain being optionally interrupted by oxygen or sulfur atoms, an alkyl- or arylamino moiety, NH—CO or CO—NH; a 1,4-phenylene; or a 1,4-phenylenemethylene moiety, said moiety being optionally substituted by at least one linear or branched alkyl or alkoxy group and/or halogen atom; and wherein $R_C$ is a linear or branched acyclic, cyclic or multicyclic moiety, said moiety being optionally unsaturated and/or substituted by at least one hydrogen, $OR^i$, amino, alkyl- or dialkylamino, $NHCOR^i$, halogen, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein $R^i$ is hydrogen, CHO, $COOR^{ii}$, or a substituted or unsubstituted linear or branched chain alkyl, arylalkyl or aryl group aryl, alkylaryl or arylalkyl; wherein if $R_C$ is cyclic, said moiety is optionally aromatic and/or heterocyclic; or if multicyclic, said moiety is optionally a fused multicyclic, fully or partially aromatic and/or heterocyclic; which comprises: (a) O-silylating HO—$R_C$ with $X_2SiR_AR_B$, wherein X is a halogen, in the presence of a base under conditions to form a halosilyl compound having the structure: $XSiR_AR_B$—$OR_C$; and (b) coupling the halosilyl compound formed in step (a) with a polymeric alcohol support in the presence of a base under conditions to form the polymer-linked composition.

Another object of the present invention is to provide a method of preparing a compound having the structure $R_C$—OH wherein $R_C$ is a linear or branched acyclic, cyclic or multicyclic moiety, said moiety being optionally unsaturated and/or substituted by at least one hydrogen, $OR^i$, amino, alkyl- or dialkylamino, $NHCOR^i$, halogen, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein $R^i$ is hydrogen, CHO, $COOR^{ii}$, or a substituted or unsubstituted linear or branched chain alkyl, arylalkyl or aryl group aryl, alkylaryl or arylalkyl; wherein if $R_C$ is cyclic, said moiety is optionally aromatic and/or heterocyclic; or if multicyclic, said moiety is optionally a fused multicyclic, fully or partially aromatic and/or heterocyclic; which method comprises:

(a) preparing a polymer-linked composition having the structure:

wherein $R_A$ and $R_B$ are each independently a $C_{1-6}$ linear or $C_{3-10}$ branched chain alkyl or an aryl group; wherein Ⓟ is a polymeric support; wherein L is a linker selected from the group consisting of a single bond; a saturated or unsaturated oligomethylene chain, said oligomethylene chain being optionally interrupted by oxygen or sulfur atoms, an alkyl- or arylamino moiety, NH—CO or CO—NH; a 1,4-phenylene; or a 1,4-phenylenemethylene moiety, said moiety being optionally substituted by at least one linear or branched alkyl or alkoxy group and/or halogen atom; and (b) treating the polymer-linked composition with a cleaving reagent under suitable conditions to form $R_C$—OH.

DETAILED DESCRIPTION OF THE INVENTION

As used herein, the term "linear or branched chain alkyl" encompasses, but is not limited to, methyl, ethyl, propyl, isopropyl, t-butyl, sec-butyl, cyclopentyl or cyclohexyl. The alkyl group may contain one carbon atom or as many as fourteen carbon atoms, but preferably contains one carbon atom or as many as nine carbon atoms, and may be substituted by various groups, which include, but are not limited to, acyl, aryl, alkoxy, aryloxy, carboxy, hydroxy, carboxamido and/or N-acylamino moieties.

As used herein, the term "alkoxycarbonyl" encompasses, but is not limited to, methoxycarbonyl, ethoxycarbonyl, propoxycarbonyl, n-butoxycarbonyl, benzyloxycarbonyl, hydroxypropylcarbonyl, aminoethoxy-carbonyl, sec-butoxycarbonyl and cyclopentyloxycarbonyl. Examples of "acyl" groups include, but are not limited to, formyl, acetyl, propionyl, butyryl and penanoyl. Examples of "alkoxy" groups include, but are not limited to, methoxy, ethoxy, propoxy, n-butoxy, sec-butoxy and cyclopentyloxy.

As used herein, an "aryl" encompasses, but is not limited to, a phenyl, pyridyl, pyrryl, indolyl, naphthyl, thiophenyl or furyl group, each of which may be substituted by various groups, which include, but are not limited to, acyl, aryl alkoxy, aryloxy, carboxy, hydroxy, carboxamido or N-acylamino moieties. Examples of aryloxy groups include, but are not limited to, a phenoxy, 2-methylphenoxy, 3-methylphenoxy and 2-naphthoxy. Examples of acyloxy groups include, but are not limited to, acetoxy, propanoyloxy, butyryloxy, pentanoyloxy and hexanoyloxy.

As used herein, the term "acyclic" refers to any linear organic molecule. Examples include linear alkyl chains, such as oligomethylenes, which may be substituted or unsubstituted by such functional groups as alkoxy, aryl, aryloxy, acyloxy or benzyl, or which may be saturated or partially or fully unsaturated; or linear alkyl chains, interrupted by heteroatoms, such as oxygen or sulfur atoms, NH or N—CONH$_2$.

As used herein, "cyclic moiety" refers to any isolated ring system. Examples include rings of varying size, e.g., containing three, four, five, six, seven or eight ring atoms, but may also include macrocyclic rings, containing ten or more ring atoms. Such rings may be substituted or unsubstituted, as for acyclics, and may be saturated or partially or fully unsaturated. In addition, heteroatoms such as sulfur, oxygen, NH, etc., may interrupt the ring. "Heterocyclic" rings include, for example, pyrrole, pyridine, thiophene, furan, thiofuran, dihydrofuran, etc. Common examples of non-heterocylics include cyclopentane, cyclohexane, cyclopentene, cyclohexene, benzene, and the like.

As used herein, "multicyclic moiety" refers to any of the cyclic moieties linked together to form chains of ring systems, such as biphenyl, or cyclic moieties may be fused together to form such systems as indane, decalin, naphthalene, tetrahydronaphthalene, anthracene, and the like. Such rings may be substituted or unsubstituted, and may be saturated or partially or fully unsaturated. Also, heteroatoms such as sulfur, oxygen, NH, etc., may interrupt any one of the rings. Examples of heterocyclic multicyclics include indole, benzofuran, bipyridine, tetraphenylporphyrin, etc.

The subject invention provides a polymer-linked composition having the structure:

wherein $R_A$ and $R_B$ are each independently a $C_{1-6}$ linear or $C_{3-10}$ branched chain alkyl or an aryl group; wherein Ⓟ is a polymeric support; wherein L is a linker selected from the group consisting of a single bond; a saturated or unsaturated oligomethylene chain, said oligomethylene chain being optionally interrupted by oxygen or sulfur atoms, an alkyl- or arylamino moiety, NH—CO or CO—NH; a 1,4-phenylene; or a 1,4-phenylenemethylene moiety, said moiety being optionally substituted by at least one linear or branched alkyl or alkoxy group and/or halogen atom; and wherein $R_C$ is a linear or branched acyclic, cyclic or multicyclic moiety, said moiety being optionally unsaturated and/or substituted by at least one hydrogen, $OR^i$, amino, alkyl- or dialkylamino, $NHCOR^i$, halogen, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein $R^i$ is hydrogen, CHO, $COOR^{ii}$, or a substituted or unsubstituted linear or branched chain alkyl, arylalkyl or aryl group aryl, alkylaryl or arylalkyl; wherein if $R_C$ is cyclic, said moiety is optionally aromatic and/or heterocyclic; or if multicyclic, said moiety is optionally a fused multicyclic, fully or partially aromatic and/or heterocyclic.

In one embodiment, the invention provides a polymer-linked composition as shown above wherein $R_C$ is a carbohydrate having the structure:

wherein a, b, c, d, e and f are independently 0, 1, 2 or 3; wherein $R_1$, $R_2$, $R_3$, $R_4$, $R_5$ and $R_6$ are independently hydrogen, OH, $OR^i$, amino, $NHCOR^i$, halogen, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein $R^i$ is hydrogen, CHO, $COOR^{ii}$, or a substituted or unsubstituted linear or branched chain alkyl, arylalkyl or aryl group; wherein $R^{ii}$ is hydrogen, a substituted or unsubstituted linear or branched chain alkyl, arylalkyl or aryl group; and wherein the dotted line represents an optional double bond; wherein when said double bond is present, $R_1$ and $R_2$ are not both OH or amino.

In a certain embodiment, the invention provides a polymer-linked composition as shown wherein $R_A$ and $R_B$ are each isopropyl. In another embodiment, the invention provides a polymer-linked composition wherein L is 1,4-phenylenemethylene, and the composition has the structure:

The present invention also provides a polymer-linked composition wherein $R_C$ is a carbohydrate having the structure:

wherein a, b, c, d, e, f, g, h, i, j, k, m, n, p, q, x and y are independently 0, 1, 2 or 3; wherein $R_0$, $R_1$, $R_2$, $R_3$, $R_4$, $R_5$, $R_6$, $R_7$, $R_8$, $R_9$, $R_{10}$, $R_{11}$ and $R_{12}$ are each independently hydrogen, OH, $OR^i$, $NH_2$, $NHCOR^i$, F, $CH_2OH$, $CH_2OR^i$, a substituted or unsubstituted linear or branched chain alkyl, (mono-, di- or tri)hydroxyalkyl, (mono-, di- or tri) acyloxyalkyl, arylalkyl or aryl group; wherein $R^i$ is hydrogen, CHO, $COOR^{ii}$, or a substituted or unsubstituted linear or branched chain alkyl, arylalkyl or aryl group or a saccharide moiety having the structure:

wherein Y and Z are independently NH or O; wherein r, s, t, u, v, w, z and z' are each independently 0, 1 or 2; wherein $R_x$ is hydrogen, a linear or branched chain alkyl, acyl, arylalkyl or aryl group; wherein $R_{13}$, $R_{14}$, $R_{15}$, $R_{16}$, $R_{17}$, $R_{18}$ and $R_{19}$ are each independently hydrogen, OH, $OR^{iii}$, $NH_2$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri)acyloxyalkyl, arylalkyl or aryl group; wherein $R_{16}$ is hydrogen, COOH, $COOR^{ii}$, $CONHR^{ii}$, a substituted or unsubstituted linear or branched chain alkyl or aryl group; wherein $R^{iii}$ is hydrogen, CHO, $COOR^{iv}$, or a substituted or unsubstituted linear or branched chain alkyl, arylalkyl or aryl group; and wherein $R^{ii}$ and $R^{iv}$ are each independently H, or a substituted or unsubstituted linear or branched chain alkyl, arylalkyl or aryl group; wherein the dotted line represents an optional double bond; wherein when said double bond is present, $R_0$ and $R_3$ are not both OH or amino; and wherein said carbohydrate is optionally linked to an amino acyl or hydroxy acyl residue of a psubstructure by substitution of a side group or terminal group substituent thereof selected from the group consisting of OH, COOH and $NH_2$, said substructure being:

wherein m, n, p and q are 0, 1, 2 or 3 such that $m+n+p+q \leq 6$; wherein A, B, C, D, E and F are independently amino acyl or hydroxy acyl residues wherein A is N- or O-terminal and is either a free amine or an ammonium form when A is amino acyl or a free hydroxy when A is hydroxy acyl, or A is alkylated, arylated or acylated; and wherein F is either a free carboxylic acid, primary carboxamide, mono- or dialkyl carboxamide, mono- or diaryl-carboxamide, linear or branched chain (carboxy)alkyl carboxamide, linear or branched chain (alkoxycarbonyl)alkylcarboxamide, linear or branched chain (carboxy)arylalkylcarboxamide, linear or branched chain (alkoxycarbonyl)-alkylcarboxamide, an oligoester fragment comprising from 2 to about 20 hydroxy acyl residues, a peptidic fragment comprising from 2 to about 20 amino acyl residues, or a linear or branched chain alkyl or aryl carboxylic ester.

The invention further provides a polymer-linked composition wherein $R_C$ has the structure of a cell surface epitope. In a certain embodiment, the epitope is $Le^a$, $Le^b$, $Le^x$, or $Le^y$. In another embodiment; the epitope is MBr1, a truncated MBr1 pentasaccharide or a truncated MBr1 tetrasaccharide.

In addition, the invention provides specific polymer-linked compositions wherein $R_C$ is a saccharide having the structure:

Other polymer-linked compositions provided by the invention include those wherein $R_C$ is a saccharide having the structure:

The present invention provides a method for preparing a polymer-linked composition having the structure:

wherein $R_A$ and $R_B$ are each independently a $C_{1-6}$ linear or $C_{3-10}$ branched chain alkyl or an aryl group; wherein Ⓟ is a polymeric support; wherein L is a linker selected from the group consisting of a single bond; a saturated or unsaturated oligomethylene chain, said oligomethylene chain being optionally interrupted by oxygen or sulfur atoms, an alkyl- or arylamino moiety, NH—CO or CO—NH; a 1,4-phenylene; or a 1,4-phenylenemethylene moiety, said moi- ety being optionally substituted by at least one linear or branched alkyl or alkoxy group and/or halogen atom; and wherein $R_C$ is a linear or branched acyclic, cyclic or multicyclic moiety, said moiety being optionally unsaturated and/or substituted by at least one hydrogen, $OR^i$, amino, alkyl- or dialkylamino, $NHCOR^i$, halogen, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein $R^i$ is hydrogen, CHO, $COOR^{ii}$, or a substituted or unsubstituted linear or branched chain alkyl, arylalkyl or aryl group aryl, alkylaryl or arylalkyl; wherein if $R_C$ is cyclic, said moiety is optionally aromatic and/or heterocyclic; or if multicyclic, said moiety is optionally a fused multicyclic, fully or partially aromatic and/or heterocyclic; which comprises: (a) O-silylating $HO—R_C$ with $X_2SiR_AR_B$, wherein X is a halogen, in the presence of a base under conditions to form a halosilyl compound having the structure: $XSiR_AR_B—OR_C$; and (b) coupling the halosilyl compound formed in step (a) with a polymeric alcohol support in the presence of a base under conditions to form the polymer-linked composition.

In one embodiment, the invention provides a method as described wherein the base is imidazole. In another embodiment, the invention provides a method wherein $R_C$ is a carbohydrate having the structure:

$R_{18}$ and $R_{19}$ are each independently hydrogen, OH, $OR^{iii}$, $NH_2$, $NHCOR^{iii}$, F, $CH_2OH$, $CH_2OR^{iii}$, or a substituted or unsubstituted linear or branched chain alkyl,(mono-, di- or tri)hydroxyalkyl, (mono-, di- or tri)acyloxyalkyl, arylalkyl or aryl group; wherein $R_{16}$ is hydrogen, COOH, $COOR^{ii}$, $CONHR^{ii}$, a substituted or unsubstituted linear or branched chain alkyl or aryl group; wherein $R^{iii}$ is hydrogen, CHO, $COOR^{iv}$, or a substituted or unsubstituted linear or branched chain alkyl, arylalkyl or aryl group; and wherein $RR^{ii}$ and $R^{iv}$ are each independently H, or a substituted or unsubstituted linear or branched chain alkyl, arylalkyl or aryl group; wherein the dotted line represents an optional double bond; wherein when said double bond is present, $R_0$ and $R_3$ are not both OH or amino; and wherein said carbohydrate is optionally linked to an amino acyl or hydroxy acyl residue of a substructure by substitution of a side group or terminal group substituent thereof selected from the group consisting of OH, COOH and $NH_2$, said substructure being:

wherein m, n, p and q are 0, 1, 2 or 3 such that $m+n+p+q \leq 6$; wherein A, B, C, D, E and F are independently amino acyl or hydroxy acyl residues wherein A is N- or O-terminal and is either a free amine or an ammonium form when A is amino acyl or a free hydroxy when A is hydroxy acyl, or A is alkylated, arylated or acylated; and wherein F is either a free wherein a, b, c, d, e, f, g, h, i, j, k, m, n, p, q, x and y are each independently 0, 1, 2 or 3; wherein $R_0$, $R_1$, $R_2$, $R_3$, $R_4$, $R_5$, $R_6$, $R_7$, $R_8$, $R_9$, $R_{10}$, $R_{11}$ and $R_{12}$ are each independently hydrogen, OH, $OR^i$, $NH_2$, $NHCOR^i$, F, $CH_2OH$, $CH_2OR^i$, a substituted or unsubstituted linear or branched chain alkyl, (mono-, di- or tri)hydroxyalkyl, (mono-, di- or tri) acyloxyalkyl, arylalkyl or aryl group; wherein $R^i$ is hydrogen, CHO, $COOR^{ii}$, or a substituted or unsubstituted linear or branched chain alkyl, arylalkyl or aryl group or a saccharide moiety having the structure:

wherein Y and Z are each independently NH or O; wherein r, s, t, u, v, w, z and z' are each independently 0, 1 or 2; wherein $R_x$ is hydrogen, a linear or branched chain alkyl, acyl, arylalkyl or aryl group; wherein $R_{13}$, $R_{14}$, $R_{15}$ $R_{16}$, $R_{17}$, carboxylic acid, primary carboxamide, mono- or dialkyl carboxamide, mono- or diaryl-carboxamide, linear or branched chain (carboxy)alkyl carboxamide, linear or branched chain (alkoxycarbonyl)alkyl-carboxamide, linear or branched chain (carboxy)arylalkylcarboxamide, linear or branched chain (alkoxycarbonyl)-alkylcarboxamide, an oligoester fragment comprising from 2 to about 20 hydroxy acyl residues, a peptidic fragment comprising from 2 to about 20 amino acyl residues, or a linear or branched chain alkyl or aryl carboxylic ester.

The method may also be practiced wherein $R_C$ is a carbohydrate having the structure:

wherein a, b, c, d, e and f are each independently 0, 1, 2 or 3; wherein $R_1$, $R_2$, $R_3$, $R_4$, $R_5$ and $R_6$ are independently hydrogen, OH, $OR^i$, amino, $NHCOR^i$, halogen, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein $R^i$ is hydrogen, CHO, $COOR^{ii}$, or a substituted or unsubstituted linear or branched chain alkyl, arylalkyl or aryl group; wherein $R^{ii}$ is hydrogen, a substituted or unsubstituted linear or branched chain alkyl, arylalkyl or aryl group; and wherein the dotted line represents an optional double bond; wherein when said double bond is present, $R_1$ and $R_2$ are not both OH or amino. In a certain preferred embodiment, the invention provides a method wherein $R_A$ and $R_B$ are each isopropyl. Additionally, the method is favorably carried out where L is 1,4-phenylenemethylene, and the composition has the structure:

In another embodiment, the invention provides a method as disclosed herein wherein $R_C$ is a carbohydrate having the structure:

In a certain embodiment, the method of the invention is carried out wherein $R_C$ is a carbohydrate having the structure:

The above method may be performed using a polymeric alcohol support selected from a wide variety of polymeric supports. For example, poly((p-hydroxymethylphenyl) ethylene), poly((p-hydroxyphenyl)ethylene) and poly ((hydroxymethyl)ethylene are useful for the purpose. Poly ((p-hydroxymethylphenyl)ethylene), also known as Wang resin, is particularly preferred. The polymeric alcohol resin is conveniently and favorably used in bead form. The method is efficiently performed wherein X is a halogen, or triflate; chlorine is a preferred halogen.

The present invention also provides a method of preparing a compound having the structure $R_C$—OH wherein $R_C$ is a linear or branched acyclic, cyclic or multicyclic moiety, said moiety being optionally unsaturated and/or substituted by at least one hydrogen, $OR^i$, amino, alkyl- or dialkylamino, $NHCOR^i$, halogen, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein $R^i$ is hydrogen, CHO, $COOR^{ii}$, or a substituted or unsubstituted linear or branched chain alkyl, arylalkyl or aryl group aryl, alkylaryl or arylalkyl; wherein if $R_C$ is cyclic, said moiety is optionally aromatic and/or heterocyclic; or if multicyclic, said moiety is optionally a fused multicyclic, fully or partially aromatic and/or heterocyclic; which method comprises:

(a) preparing a polymer-linked composition having the structure:

wherein $R_A$ and $R_B$ are each independently a $C_{1-6}$ linear or $C_{3-10}$ branched chain alkyl or an aryl group; wherein ⓟ is a polymeric support; wherein L is a linker selected from the group consisting of a single bond; a saturated or unsaturated oligomethylene chain, said oligomethylene chain being optionally interrupted by oxygen or sulfur atoms, an alkyl- or arylamino moiety, NH—CO or CO—NH; a 1,4-phenylene; or a 1,4-phenylenemethylene moiety, said moiety being optionally substituted by at least one linear or branched alkyl or alkoxy group and/or halogen atom; and (b) treating the polymer-linked composition with a cleaving reagent under suitable conditions to form $R_C$—OH.

In one embodiment, the method is favorably practiced wherein the cleaving agent is a fluoride reagent. In particular, the fluoride reagent is a tetra-alkylammonium fluoride, such as tetra-n-butylammonium fluoride, or pyridinium fluoride.

The method disclosed above may be applied wherein $R_C$ is a carbohydrate having the structure:

wherein a, b, c, d, e, f, g, h, i, j, k, m, n, p, q, x and y are each independently 0, 1, 2 or 3; wherein $R_0$, $R_1$, $R_2$, $R_3$, $R_4$, $R_5$, $R_6$, $R_7$, $R_8$, $R_9$, $R_{10}$, $R_{11}$ and $R_{12}$ are each independently hydrogen, OH, $OR^i$, $NH_2$, $NHCOR^i$, F, $CH_2OH$, $CH_2OR^i$, a substituted or unsubstituted linear or branched chain alkyl, (mono-, di- or tri)hydroxyalkyl, (mono-, di- or tri) acyloxyalkyl, arylalkyl or aryl group; wherein $R^i$ is hydrogen, CHO, COOR$^{ii}$, or a substituted or unsubstituted linear or branched chain alkyl, arylalkyl or aryl group or a saccharide moiety having the structure:

wherein Y and Z are each independently NH or O; wherein r, s, t, u, v, w, z and z' are each independently 0, 1 or 2; wherein R$_x$ is hydrogen, a linear or branched chain alkyl, acyl, arylalkyl or aryl group; wherein R$_{13}$, R$_{14}$, R$_{15}$ R$_{16}$, R$_{17}$, R$_{18}$ and R$_{19}$ are each independently hydrogen, OH, OR$^{iii}$, NH$_2$, NHCOR$^{iii}$, F, CH$_2$OH, CH$_2$OR$^{iii}$, or a substituted or unsubstituted linear or branched chain alkyl,(mono-, di- or tri)hydroxyalkyl, (mono-, di- or tri)acyloxyalkyl, arylalkyl or aryl group; wherein R$_{16}$ is hydrogen, COOH, COOR$^{ii}$, CONHR$^{ii}$, a substituted or unsubstituted linear or branched chain alkyl or aryl group; wherein R$^{iii}$ is hydrogen, CHO, COOR$^{iv}$, or a substituted or unsubstituted linear or branched chain alkyl, arylalkyl or aryl group; and wherein R$^{ii}$ and R$^{iv}$ are each independently H, or a substituted or unsubstituted linear or branched chain alkyl, arylalkyl or aryl group; wherein the dotted line represents an optional double bond; wherein when said double bond is present, R$_0$ and R$_3$ are not both OH or amino; and wherein said carbohydrate is optionally linked to an amino acyl or hydroxy acyl residue of a substructure by substitution of a side group or terminal group substituent thereof selected from the group consisting of OH, COOH and NH$_2$, said substructure being:

wherein m, n, p and q are 0, 1, 2 or 3 such that m+n+p+q≦6; wherein A, B, C, D, E and F are independently amino acyl or hydroxy acyl residues wherein A is N- or O-terminal and is either a free amine or an ammonium form when A is amino acyl or a free hydroxy when A is hydroxy acyl, or A is alkylated, arylated or acylated; and wherein F is either a free carboxylic acid, primary carboxamide, mono- or dialkyl carboxamide, mono- or diaryl-carboxamide, linear or branched chain (carboxy)alkyl carboxamide, linear or branched chain (alkoxycarbonyl)alkylcarboxamide, linear or branched chain (carboxy)arylalkylcarboxamide, linear or branched chain (alkoxycarbonyl)-alkylcarboxamide, an oligoester fragment comprising from 2 to about 20 hydroxy acyl residues, a peptidic fragment comprising from 2 to about 20 amino acyl residues, or a linear or branched chain alkyl or aryl carboxylic ester.

In one embodiment, R$_C$ is a carbohydrate having the structure:

wherein a, b, c, d, e and f are each independently 0, 1, 2 or 3; wherein R$_1$, R$_2$, R$_3$, R$_4$, R$_5$ and R$_6$ are independently hydrogen, OH, OR$^i$, amino, NHCOR$^i$, halogen, CH$_2$OH, CH$_2$OR$^i$, a substituted or unsubstituted linear or branched chain alkyl, (mono-, di- or tri)hydroxyalkyl, (mono-, di- or tri)acyloxyalkyl, arylalkyl or aryl group; wherein R$^i$ is hydrogen, CHO, COOR$^{ii}$, or a substituted or unsubstituted linear or branched chain alkyl, arylalkyl or aryl group; wherein R$^{ii}$ is hydrogen, a substituted or unsubstituted linear or branched chain alkyl, arylalkyl or aryl group; and wherein the dotted line represents an optional double bond; wherein when said double bond is present, R$_1$ and R$_2$ are not both OH or amino.

In another embodiment, R$_A$ and R$_B$ are each isopropyl. In yet another embodiment, L is 1,4-phenylenemethylene.

The glycoconjugates prepared by the silylene-based linking method disclosed herein are especially useful as cell surface epitopes specific to certain tumor lines which allow the development of immunity in subjects to which such glycoconjugates are administered. Examples of such utility are provided in related copending applications cited herein, the contents of which are incorporated herein by reference.

Throughout this application, various publications are referred to, each of which is hereby incorporated by reference in its entirety into this application to more fully describe the state of the art to which the invention pertains.

The present invention will be better understood from the Experimental Details which follow. However, one skilled in the art will readily appreciate that the specific methods and results discussed are merely illustrative of the invention as described in the claims which follow thereafter.

Experimental Details

General Procedures

All air- and moisture-sensitive reactions were performed in a flame-dried apparatus under an argon atmosphere unless otherwise noted. Air-sensitive liquids and solutions were transferred via syringe or cannula. Wherever possible, reactions were monitored by thin-layer chromatography (TLC). Gross solvent removal was performed in vacuum under aspirator vacuum on a Buchi rotary evaporator, and trace solvent was removed on a high vacuum pump at 0.1–0.5 mmHg.

Melting points (mp) were uncorrected and performed in soft glass capillary tubes using an Electrothermal series IA9100 digital melting point apparatus. Infrared spectra (IR) were recorded using a Perkin-Elmer 1600 series Fourier-Transform instrument. Samples were prepared as neat films on NaCl plates unless otherwise noted. Absorption bands are reported in wavenumbers (cm$^1$). Only relevant, assignable bands are reported.

Proton nuclear magnetic resonance ($^1$H NMR) spectra were determined using a Bruker AMX-400 spectrometer at 400 MHz. Chemical shifts are reported in parts per million (ppm) downfield from tetramethylsilane (TMS; δ=0 ppm) using residual CHCl$_3$ as a lock reference (δ=7.25 ppm). Multiplicities are abbreviated in the usual fashion: s=singlet; d=doublet; t=triplet; q=quartet; m=multiplet; br=broad. Carbon nuclear magnetic resonance ($^{13}$C NMR) spectra were performed on a Bruker AMX-400 spectrometer at 100 MHz with composite pulse decoupling. Samples were prepared as with $^1$H NMR spectra, and chemical shifts are reported relative to TMS (0 ppm); residual CHCl$_3$ was used as an internal reference (δ=77.0 ppm). All high resolution mass spectral (HRMS) analyses were determined by electron impact ionization (EI) on a JEOL JMS-DX 303HF mass spectrometer with perfluorokerosene (PFK) as an internal standard. Low resolution mass spectra (MS) were determined by either electron impact ionization (EI) or chemical ionization (CI) using the indicated carrier gas (ammonia or methane) on a Delsi-Nermag R-10-10 mass spectrometer.

For gas chromatography/mass spectra (GCMS), a DB-5 fused capillary column (30 m, 0.25 mm thickness) was used with helium as the carrier gas. Typical conditions used a temperature program from 60–250° C. at 40° C./min.

Thin layer chromatography (TLC) was performed using precoated glass plates (silica gel 60, 0.25 mm thickness). Visualization was done by illumination with a 254 nm UV lamp, or by immersion in anisaldehyde stain (9.2 mL p-anisaldehyde in 3.5 mL acetic acid, 12.5 mL conc. sulfuric acid and 338 mL 95.% ethanol (EtOH)) and heating to colorization. Flash silica gel chromatography was carried out according to the standard protocol.

Unless otherwise noted, all solvents and reagents were commercial grade and were used as received, except as indicated hereinbelow, where solvents were distilled under argon using the drying methods listed in parentheses: $CH_2Cl_2$ ($CaH_2$); benzene ($CaH_2$); THF (Na/ketyl); $Et_2O$ (Na/ketyl); diisopropylamine ($CaH_2$).

| Abbreviations | |
|---|---|
| TLC | thin layer chromatography |
| EtOAc | ethyl acetate |
| TIPS | triisopropylsilyl |
| PMB | p-methoxybenzyl |
| Bn | benzyl |
| Ac | acetate |
| hex | hexane |
| THF | tetrahydrofuran |
| coll | collidine |
| LiHMDS | lithium hexamethyldisilazide |
| DMF | N,N-dimethylformamide |
| DMAP | 2-dimethylaminopyridine |
| DDQ | 2,3-dichloro-5,6-dicyano-1,4-benzoquinone |
| TBAF | tetra-n-butylammonium fluoride |
| M.S. | molecular sieves |
| r.t. | room temperature |
| r.b. | round bottom flask |

Methods for preparing carbohydrate domains and glycoconjugates based on a solid-phase methodology have been disclosed in U.S. Pat. No. 5,543,505, U.S. Serial Nos. 60/043,713, 08/477,776, 08/213,053, 08/430,355, 08/506,251 and in PCT International Application Nos. PCTUS95/03273 and PCT/US96/10229, the contents of which are incorporated herein by reference.

EXAMPLE 1
Loading of 3,6-Di-benzyl Glucal

Figure 1A:
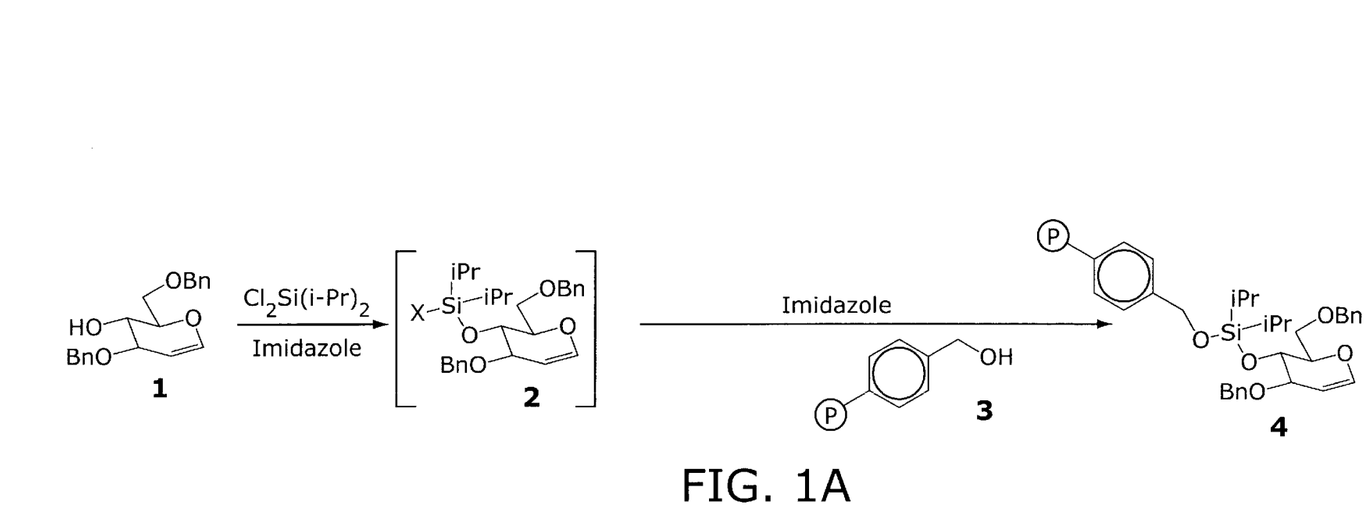
FIG. 1(a) illustrates the preparation of polymer-linked composition 4. Hydroxymethyl (Wang) resin consisted of 0.96 mmole/gram benzylalcohol monomer with loading from 0.19–0.25 mmole/gram, depending on substrate used.

The 4-position is sterically shielded, and, consequently, the hydroxyl relatively unreactive. Exposure to one equivalent of the dichlorodiisoproyl silane in methylene chloride and five equivalents of imidazole revealed intermediate 2 cleanly by thin layer chromatographic analysis after just 30 minutes. (See FIG. 1.) This material was then reacted with the benzyl hydroxy polymer 3 (commercial hydroxymethyl (Wang) resin) in dichloromethane for 20 h, resulting in the linked glycal 4. The unreacted sites could then be capped by reaction with imidazole and diisopropyldichlorosilane, followed by methanol. Similar processes were carried out with a variety of carbohydrate systems, many of which were sterically demanding and showed similarly good results. (See FIG. 2.)

Protocol

In a 25 mL round bottom with stir bar was weighed the imidazole (2.21 g, 32.45 mmol) and this was diluted with 10 mL of $CH_2Cl_2$. To the imidazole solution was added the diisopropyldichlorosilane (DIPSiCl$_2$) (1.20 g, 1.18 mL, 6.49 mmol) dropwise and this was stirred for 5 min before the 3,6-dibenzoyl D-glucal (2.3 g, 6.49 mmol) in 7 mL of methylene chloride was added dropwise via cannula and this was mixed for 30 min at rt. To an oven dried 100 mL polymer flask with filter was weighed 1.62 g of Wang resin (approximately 1.62 mmol). The polymer was diluted with 2 mL of dry $CH_2Cl_2$ and allowed to swell. The mixture of glucal, imidazole and DIPSiCl$_2$ was then added to the polymer dropwise via cannula and washed in with 2 mL of $CH_2Cl_2$. The mixture was stirred for 24 h and then filtered and washed 1×20 mL of DMF, 3×20 mL of THF, 3×20 mL of $CH_2Cl_2$ and then was exposed to high vac overnight to provide a faintly yellow polymer. This material was then capped by exposing the polymer to imidazole (2.21 g, 32.45 mmol) and DIPSiCl$_2$ (1.20 g, 1.18 mL, 6.49 mmol) in 20 mL $CH_2Cl_2$ for 24 hours and then adding methanol (0.291 mg, 368 mL, 9.09 mmol) and stirring for 48 hours. This material was washed as described above to yield 2.28 g of a faintly yellow polymer 6.

EXAMPLE 2

To test the range of reaction conditions to which this system could be exposed, one of the most labile systems 8, where the polymer is linked through the primary 6-position of galactal carbonate, was used in the synthesis of a known glycopeptide 15. (See FIG. 3.)

Figure 3:
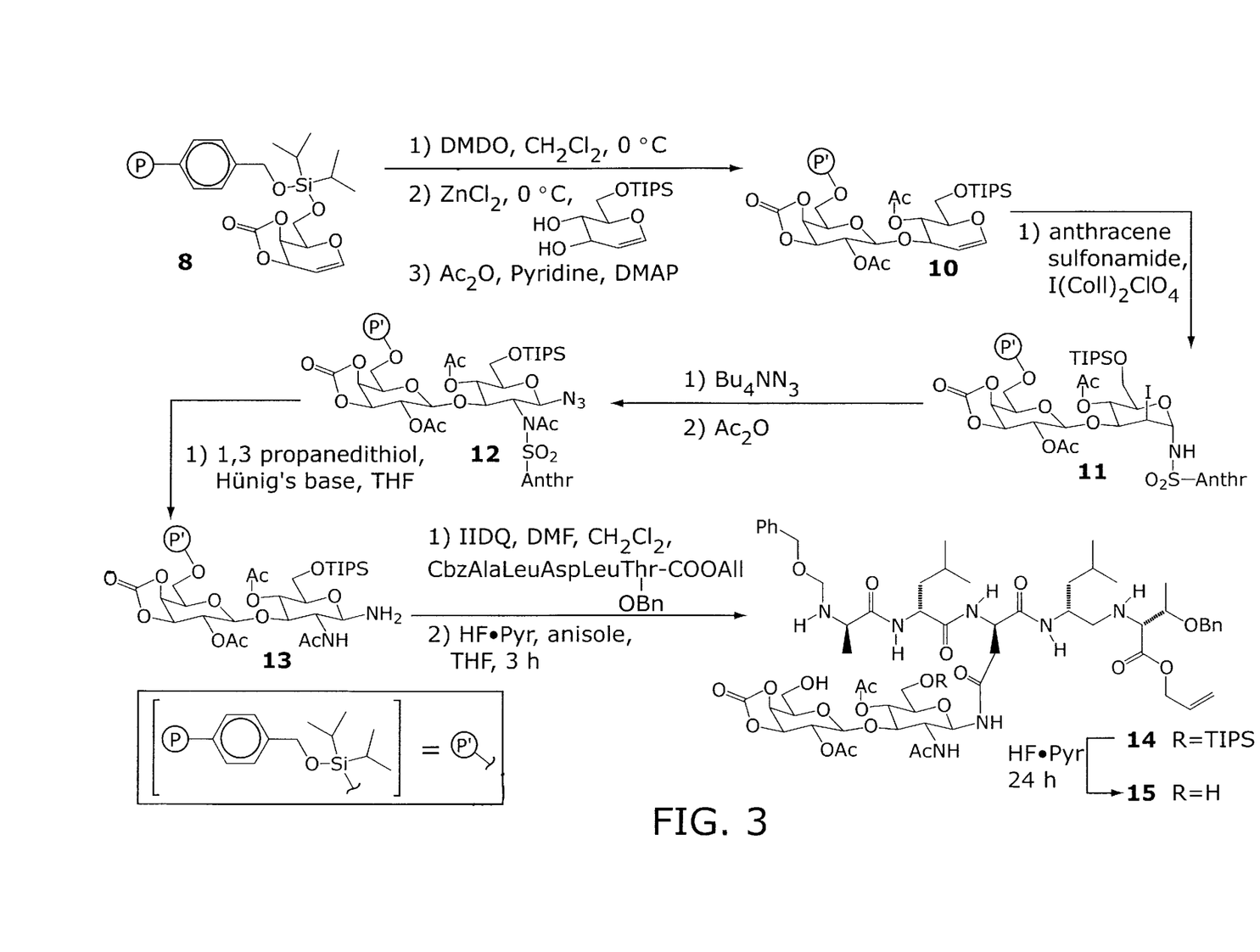
FIG. 3 illustrates the preparation of a glycopeptide by the method of the invention.

The linked galactal was reacted with dimethydioxirane (DMDO) to form an epoxide. Lewis acid-mediated epoxide opening with 6-O-TIPS-glucal provided the linked disaccharide 10. Danishefsky, S. J. et al., *Science*, 1993, 260, 1307. Acetylation of the diol and subsequent reaction with iodonium-bis-sym-collidine perchlorate and anthracene sulfonamide afforded the trans-diaxial iodosulfonamide 11. Lemieux, R. U.; Levine, S. *Can. J. Chem.* 1964, 42, 1473. Upon treatment with tetrabutylamonium azide, the iodosulfonamide underwent rearrangement to give the β-anomeric azide and sulfonamide in the C-2 position of the masked glucosamine disaccharide 11b. Brändström, A. et al., *Acta Chem. Scand.* 1974, B 28, 699. Acetylation of the sulfonamide prepared the system for subsequent deprotection of the anthracene sulfonyl group and reduction of the azide using propanedithiol and Hünig's base. Anisfeld, S. T.; Lansbury Jr., P. T. *J. Org. Chem.* 1990, 55, 5560. These mild conditions provided the stable linked disaccharide N-acetyglucosamine anomeric amine 13. Reaction with the pentapeptide in the presence of 2-isobutoxy-1-isobutoxycarbonyl-1,2-dihydroquinoline (IIDQ; Kiso, Y.; Yajima, H. *J. Chem. Soc. Chem. Commun.* 1972, 942) in DMF and methylene chloride gave the linked disaccharide pentapeptide which was readily disengaged from the support via HF.Pyr in THF (Matsuura, S.; Niu, C.-H.; Cohen, J. N. *J. Chem. Soc. Chem. Commun.* 1976, 451), providing the desired 6-O-TIPS protected glycopeptide 14. Removal of the TIPS group allowed access to the glycopeptide 15 in 44% overall yield from the loaded galactal carbonate 8. This composition was identical both spectroscopically and chromatographically to an authentic sample prepared previously.

EXAMPLE 3
Tests of Stability of Polymer-linked Compositions

Figure 4A:
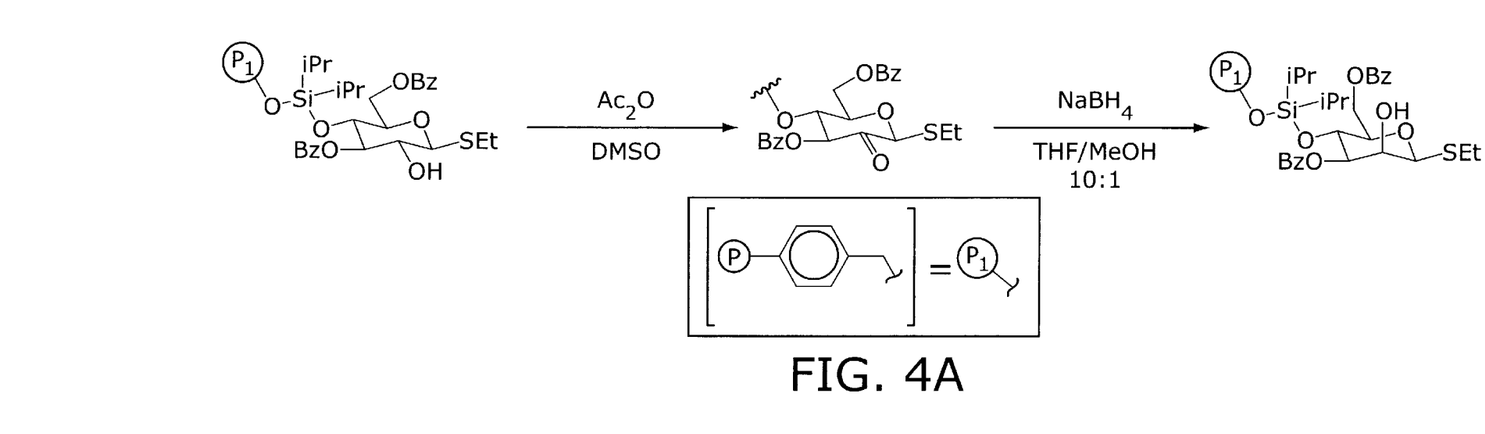
FIG. 4(a) illustrates the resistance of a polymer-linked composition to cleavage by acetic anhydride/DMSO for 5 d.
Figure 4B:
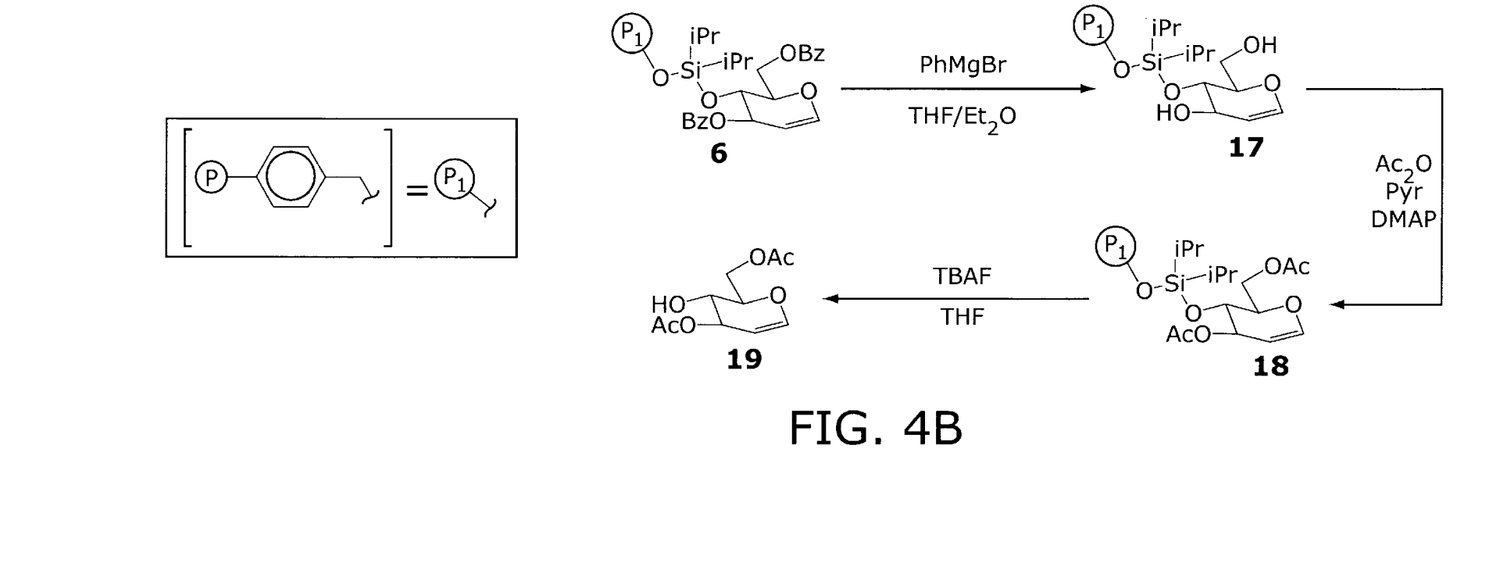
FIG. 4(b) illustrates the reaction of a phenyl Grignard reagent with a benzoylated polymer-linked composition without linker migration or cleavage (ca. 76% yield on removal from support).

The linker has also been shown to be susceptible to cleavage by tetrabutyl ammonium fluoride (TBAF) at r.t. after only a few minutes allowing for rapid, facile access to material on the polymer and simple evaluation of reaction progress by TLC. The system has demonstrated stability in the presence of Swern type oxidations, sodium borohydride reductions (FIG. 4(a)) and certain Grignard reactions (FIG. 4(b)).

EXAMPLE 4

Polymer-supported Synthesis of Gal1-3Glu-nac Pentapeptide

To 2.2 g (approximately 0.6 mmol) of polymer loaded 3,4-galactal carbonate 8 in a 100 mL polymer flask was added 20 mL methylene chloride. The mixture was cooled to 0° C. Dimethyl dioxirane (25 mL of a 0.6 molar solution in acetone, 15.0 mmol) was added dropwise via canula, stirred for 1 h at 0° C., and then the liquid was filtered, and the process repeated. The polymer was then washed with 20 mL of $CH_2Cl_2$, 20 ml of a 50/50 mixture of $CH_2Cl_2$:THF and once with THF (20 mL). The polymer was then exposed to high vacuum for 18 h. To the yellow polymer was then added 15 mL THF and cooled to 0° C. and the 6-O-TIPS glucal was then added dropwise as a solution in 5 mL of THF via cannula and washed in with 2 mL of THF. To this mixture was added $ZnCl_2$ (4 mL of a 1.0 molar solution in $Et_2O$, 4.0 mmol). The mixture was allowed to stir and come to rt over the next 28 hours. The liquid was then filtered away and the polymer was washed 2×20 mL of THF, 1×20 mL of a 50:50 mixture of $CH_2Cl_2$:THF (20 mL) and 1×20 mL of $CH_2Cl_2$, and was then exposed to high vacuum for 18 hours provided 2.4 g of a faintly yellow polymer (8a).

To a mixture of the polymer-supported disaccharide 8a (750.0 mg) swollen in 15 mL of $CH_2Cl_2$ was added $Ac_2O$ (1 mL) followed by pyridine (2 mL). After 36 h, the reaction was filtered and washed with THF (3×10 mL) and $CH_2Cl_2$ (3×10 mL) then dried udner vacuum to give 930.0 mg of polymer-bound diacetate 10: FTIR (KBr Pellet) 1820, 1761, 1647, 1370 cm-$^1$.

The anthracene sulfonamide (650 mg) and polymer-supported disaccharide glycal 10 (650 mg) were combined and dried under vacuum overnight. To a suspension of this cooled (0° C.) mixture in 6.0 mL of THF was added the iodonium(bis)sym-collidine perchlorate (1.12 g, 2.39 mmol) in one portion as a solution in 3 mL THF via canula and this was washed in with 2 mL of THF. The reaction was protected from light and stirred at 0° C. for 6.5 h, then quenched with a solution of ascorbic acid (5 g) in THF/water (22 mL/3 mL). The polymer was filtered and washed with THF/water (1:1, 3×20 mL), THF (3×20 mL) and $CH_2Cl_2$ (3×20 mL) and the resin was dried under reduced pressure to give 645 mg of resin 11: FTIR (KBr Pellet) 3482, 1820, 1 752, 1370 cm-$^1$.

To the polymer-supported iodosulfonamide 11 (645 mg) was added the tetrabutylammonium azide (690 mg, 2.907 mmol) in one portion in the glove bag under $N_2$. The resin was swollen in 19 mL of THF and after 14 h, the reaction mixture was filtered, and the residue washed with THF (3×20 mL) and $CH_2Cl_2$ (3×20 mL) which was dried under reduced pressure to give 580 mg of resin 11a an orange resin that emited at a deep blue color when exposed to short wave uv at 254 nm.

To the polymer-supported azide 11a (580 mg) swollen in 7.0 mL of THF was added $Ac_2O$ (1.184 g, 1.097 mL, 11.6 mmol) followed by DMAP (997.4 mg, 8.0 mmol) dissolved in 3 mL of THF and 400 µl of pyridine. The reaction was protected from light. After 24 h, the reaction was filtered and washed with THF (3×20 mL) and $CH_2Cl_2$ (3×20 mL) and the red orange resin was dried under reduced pressure to give 580 mg of resin 12 that emited at a deep blue-green color when exposed to short wave uv at 254 nm: FTIR (KBr pellet) 2116, 1820, 1752, 1370cm-$^1$.

In a polymer synthesis flask, the polymer-bound disaccharide azide 12 (580 mg) was swollen in 10 mL of DMF. To this mixture, 6.6 g (6.0 mL, 60.99 mmol) of 1,3-propane dithiol and 4.5 g (6.0 mL, 34.8 mmol) of diisopropylethyl amine were succesively added. The reaction lightened in color and after 16 h, the solvent was filtered and the resin was washed with DMF (3×20 mL) and 1.5 mL (14.9 mmol) 1,3-propane dithiol and 1.5 mL (8.6 mmol) of diisopropylethyl amine were succesively added. The reaction was stirred for an additional 24 h and then was filtered and washed with DMF (4×20 mL), THF (4×20 mL), $CH_2Cl_2$ (2×5 mL) and the resin was dried under reduced pressure to give 509.5 mg of an orange brown resin 13: FTIR (KBr pellet) 1820, 1 752, 1370 cm-$^1$.

In a polymer synthesis flask, the polymer-bound trisaccharide 13 (105.0 mg) was swollen in 1.0 mL of $CH_2Cl_2$ for 1 h at room temperature. To this mixture was added the pentapeptide CbzAlaLeuAspLeuThr(Obn)OAll (237.3 mg, 0.260 mmol) in 5 mL of $CH_2Cl_2$ and 1.0 mL DMF followed by IIDQ (Aldrich, 80 µL, 0.253 mmol) and washed in with 0.5 mL of $CH_2Cl_2$ and 0.5 mL of DMF. After 48 h, the solvent was filtered and the resin was washed with $CH_2Cl_2$ (5×5 mL), THF (1×5 mL), $CH_2Cl_2$ (3×5 mL) and the resin was dried under reduced pressure to give 98 mg of resin 13a: FTIR (KBr pellet) 1820, 1752, 1370 cm-$^1$.

In a Teflon™ flask, the polymer-bound trisaccharide-pentapeptide 13a (98 mg) and anisole (5.0µ, 0.46 mmol) were suspended in 3 mL of $CH_2Cl_2$ for 1 h at room temperature. The mixture was cooled to -10° C. (acetone/ice) and HF-pyridine (50 µL, 1.7 mmol) was slowly added. After 4 h the reaction was warmed to room temperature for 34 h. Water (5 mL) was added at -10° C. and the mixture was extracted with ethyl acetate (4×30 mL). The combined organic layers were washed twice with a mixture of brine (10 mL) and saturated $NaHCO_3$ (1–2 mL, pH 7). The organic extracts were dried over sodium sulfate, filtered over a medium porosity glass filter and concentrated. The residue was purified over RP-18 silica, eluting with 7:3 MEoH:$H_2O$ (0.1% TFA) →9:1 to give trisaccharide-pentapeptide 15 (5.9 mg): $[\alpha]^{24}_D$ -14.4 (c 0.65, $CH_2Cl_2$); FTIR (neat) 3289, 2955, 1807, 1745, 1639, 1537, 1454, 1371, 1230, 1167, 1050 cm-$^1$; $^1$H NMR (500 MHz, $CD_3OD$) d 7.38–7.26 (10H, m), 5.88 (1H, ddd, J=5.7, 10.5, 17.2 Hz), 5.31 (1H, dd, J=1.5, 17.2 Hz), 5.19 (1H, dd, J=1.5, 10.5 Hz), 5.13–5.00 (3H, m), 4.88–4.80 (2H, m), 4.71 (1H, t apparent, J=6.0 Hz), 4.64–4.58 (3H, m), 4.55 (1 H, dd, J=5.7, 13.2 Hz), 4.48 (1H, m), 4.42–4.36 (2H, m), 4.17–4.10 (2H, m), 3.97 (1H, t apparent, J=9.5 Hz), 3.92 (1H, m), 3.77 (2H, m), 3.57 (1H, m), 3.49 (2H, m), 2.74 (1H, dd, J=5.7, 15.7 Hz), 2.63 (1H, dd, J=6.9, 15.7 Hz), 2.10 (3H, s), 2.07 (3H, s), 1.96 (3H, s), 1.72–1.58 (6H, m), 1.35 (3H, d, J=7.2 Hz), 1.22 (3H, d, J=6.3 Hz), 0.94 (6H, d, J=6.4 Hz), 0.89 (6H, d, J=6.4 Hz); $^{13}$C NMR (125 MHz, $CD_3OD$) d 175.9, 175.1, 174.5, 173.9, 172.8, 172.6, 172.5, 171.8, 171.3, 170.8, 158.5, 155.5, 139.5, 138.2, 133.2, 129.5, 129.4, 129.3, 129.1, 129.0, 128.7, 101.4, 80.9, 79.9, 77.5, 77.3, 76.8, 75.8, 75.6, 75.5, 73.6, 73.5, 72.0, 70.3, 67.8, 67.0, 62.2, 61.3, 58.3, 55.5, 53.3, 52.2, 52.2, 51.2, 42.0, 41.5, 38.1, 25.9, 25.7, 23.6, 23.5, 23.3, 22.1, 21.8, 21.1, 20.8, 18.2, 16.4; HRMS (FAB) calcd for $C_{60}H_{83}N_7O_{23}Na$ 1292.5490, found 1292.5493.

Discussion

The chemical properties of the new polymer bound constructs were assessed. The transformation of 6 to 19 demonstrates that de-benzoylation can be achieved through the agency of phenylmagnesium bromide—without cleavage of the glycal from the support. After gaining access to both flanking hydroxyls (FIG. 4(b)), the polymer bound substrate could be further manipulated. Exhaustive acetylation and cleavage from the support via TBAF led to unbound diacetate 19 in greater than 75% yield from loaded 6. The system was readily cleaved using TBAF at rt, in only a few minutes.

Figure 1B:
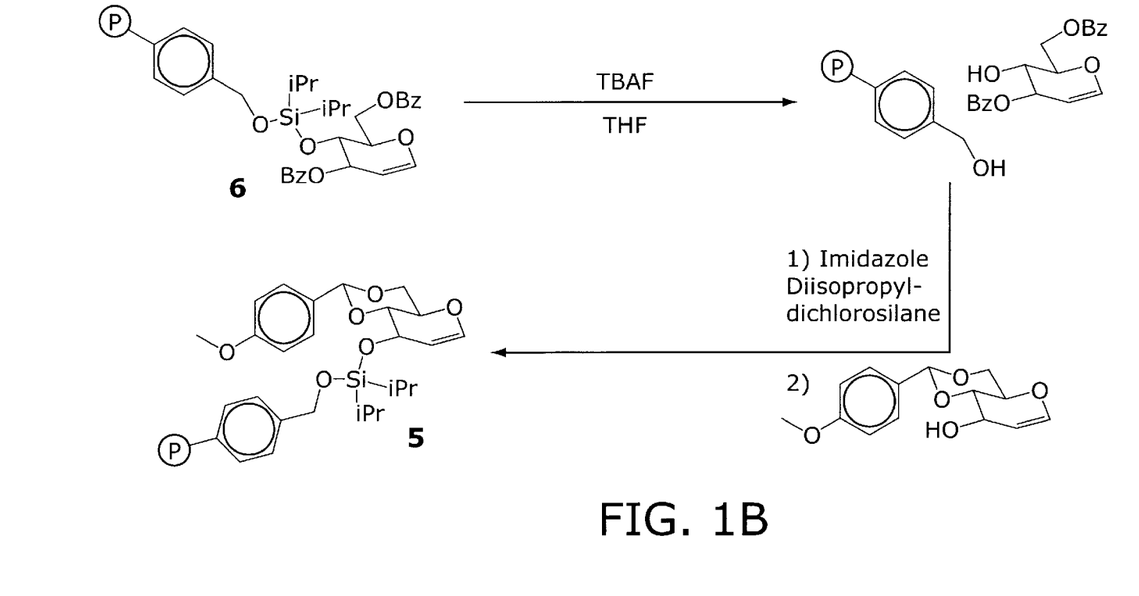
FIG. 1(b) illustrates the preparation of polymer-linked composition 5. Loading of 6 was 0.190 mmole/gram; loading of 5 was 0.120 mmole/gram.
Figure 2:
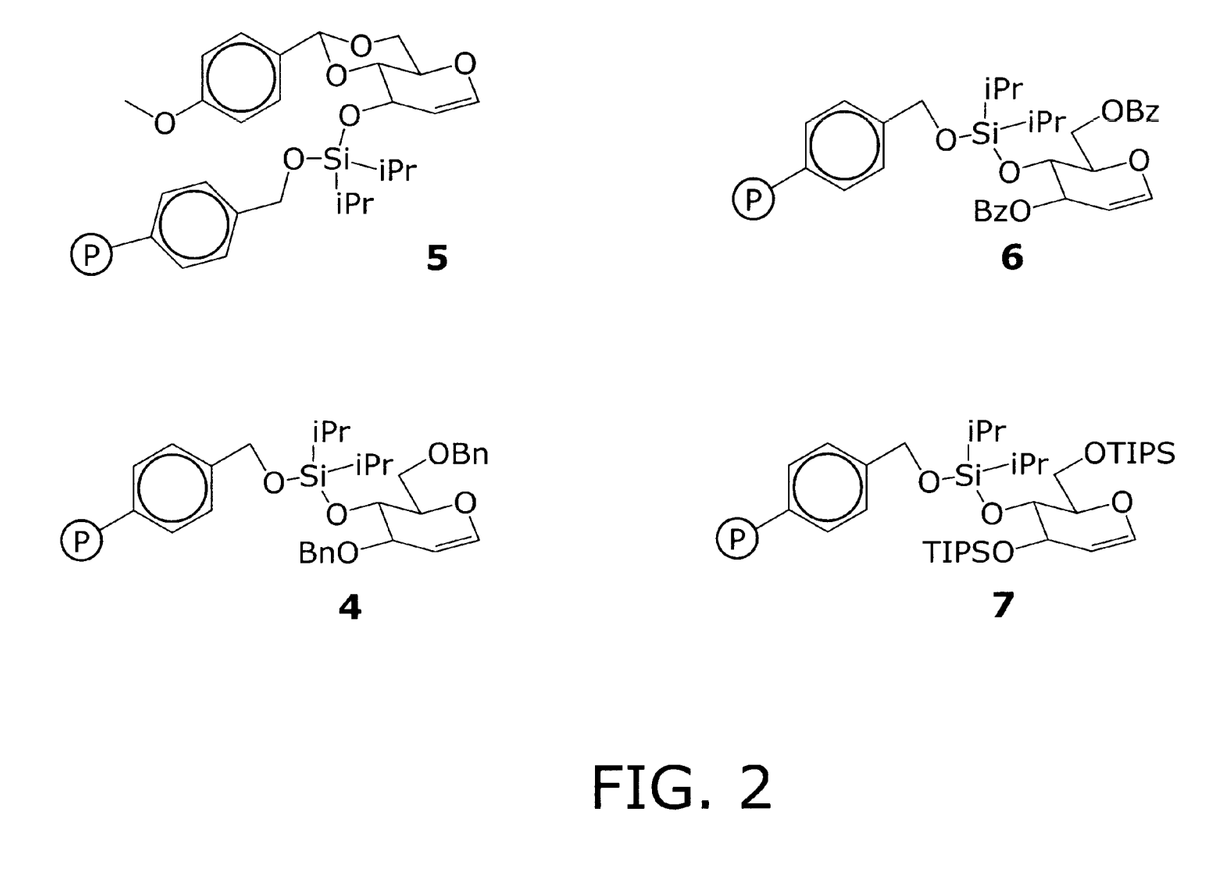
FIG. 2 illustrates polymer-linked compositions prepared by the method of the invention.

This capability allows for ready access to material on the polymer and easy evalutation of reaction progress (FIG. 1(b)). Further, use of the recovered polymer allowed for a modest loading of a second glycal, thereby demonstrating that the solid support can be recovered.

Accordingly, the present invention provides an approach utilizing a two-stage linking procedure that takes advantage of the enhanced reactivity of a di-alkyl-di-halosilane over its mono-halogenated counterpart. (Although there is some debate, the enhanced reactivity of the dichlorodialkylsilanes is believed to be primarily a steric effect with any electronic effects considered secondary.) This allows for linkage of more sterically demanding systems in the first stage, but discourages dimerizations. Furthermore, a more reactive site on the polymer would be able to access the "activated" substrate. Use of a solid support having surface hydroxyl groups, such as the commercially available hydroxymethyl modified Wang resin, provided adequate results in this capacity.

What is claimed is:

1. A method for the modification of alcohols on polymer supports comprising:

O-silylating an alcohol $R_C$—OH, wherein $R_C$ is a linear or branched acyclic, cyclic or multicyclic moiety, said moiety being optionally unsaturated and/or substituted by at least one hydrogen, $OR^i$, amino, alkyl- or dialkylamino, $NHCOR^i$, halogen, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein $R^i$ is hydrogen, CHO, $COOR^{ii}$, or a substituted or unsubstituted linear or branched chain alkyl, arylalkyl or aryl group aryl, alkylaryl or arylalkyl; wherein if $R_C$ is cyclic, said moiety is optionally aromatic and/or heterocyclic; or if multicyclic, said moiety is optionally a fused multicyclic, fully or partially aromatic and/or heterocyclic, with $X_2SiR_AR_B$, wherein X is a halogen, and $R_A$ and $R_B$ are each independently a $C_{1-6}$ linear or $C_{3-10}$ branched chain alkyl or an aryl group, in the presence of a base under conditions to form a halosilyl compound; and coupling said halosilyl compound with a polymeric alcohol support in the presence of a base under conditions to form a polymer-linked composition having the structure:

wherein $R_A$ and $R_B$ are each independently a $C_{1-6}$ linear or $C_{3-10}$ branched chain alkyl or an aryl group;

wherein (P) is a polymeric support;

wherein L is a linker selected from the group consisting of a single bond; a saturated or unsaturated oligomethylene chain, said oligomethylene chain being optionally interrupted by oxygen or sulfur atoms, an alkyl- or arylamino moiety, NH—CO or CO—NH; a 1,4-phenylene; or a 1,4-phenylenemethylene moiety, said moiety being optionally substituted by at least one linear or branched alkyl or alkoxy group and/or halogen atom, whereby said polymer-linked composition comprises at least one reactive moiety so that the polymer-linked composition can be subjected to one or more chemical reactions to generate a modified polymer-linked composition.

2. The method of claim 1, further comprising subjecting the polymer-linked composition to one or more chemical reactions to generate a modified polymer-linked composition.

3. The method of claim 2, further comprising treating said modified polymer-linked composition with a cleaving agent under suitable conditions to generate an alcohol and a reusable polymeric alcohol support.

4. The method of claim 3, further comprising the step of reusing said polymeric alcohol support, which step comprises:

O-silylating an alcohol $R_C$—OH, wherein $R_C$ is a linear or branched acyclic, cyclic or multicyclic moiety, said moiety being optionally unsaturated and/or substituted by at least one hydrogen, $OR^i$, amino, alkyl- or dialkylamino, $NHCOR^i$, halogen, $CH_2OH$, $CH_2OR^i$, a substituted or unsubstituted linear or branched chain alkyl, (mono-, di- or tri) hydroxyalkyl, (mono-, di- or tri)acyloxyalkyl, arylalkyl or aryl group, wherein $R^i$ is hydrogen, CHO, $COOR^{ii}$, or a substituted or unsubstituted linear or branched chain alkyl, arylalkyl or aryl group aryl, alkylaryl or arylalkyl; wherein $R^{ii}$ is hydrogen, a substituted or unsubstituted linear or branched chain alkyl, arylalkyl, or aryl group; wherein if $R_C$ is cyclic said moiety is optionally aromatic and/or heterocyclic; or if multicyclic, said moiety is optionally a fused multicyclic, fully or partially aromatic and/or heterocyclic, with $X_2SiR_AR_B$, wherein X is a halogen, and $R_A$ and $R_B$ are each independently a $C_{1-6}$ linear or $C_{3-10}$ branched chain alkyl or an aryl group, in the presence of a base under conditions to form a halosilyl compound; and coupling said halosilyl compound with a polymeric alcohol support in the presence of a base under conditions to form a polymer-linked composition having the structure:

wherein $R_A$ and $R_B$ are each independently a $C_{1-6}$ linear or $C_{3-10}$ branched chain alkyl or an aryl group;

wherein (P) is a polymeric support;

wherein L is a linker selected from the group consisting of a single bond; a saturated of or unsaturated oligomethylene chain, said oligomethylene chain being optionally interrupted by oxygen or sulfur atoms, an alkyl- or arylamino moiety, NH—CO or CO—NH; a 1,4-phenylene; or a 1,4-phenylenemethylene moiety, said moiety being optionally substituted by at least one linear or branched alkyl or alkoxy group and/or halogen atom, whereby said polymer-linked composition comprises at least one reactive moiety so that the polymer-linked composition can be subjected to one or more chemical reactions to generate a modified polymer-linked composition.

5. The method of claim 2, wherein said modified polymer-linked composition has the structure:

wherein $R_A$ and $R_B$ are each independently a $C_{1-6}$ linear or $C_{3-10}$ branched chain alkyl or an aryl group;

wherein (P) is a polymeric support;

wherein L is a linker selected from the group consisting of a single bond; a saturated or unsaturated oligomethylene chain, said oligomethylene chain being optionally interrupted by oxygen or sulfur atoms, an alkyl- or arylamino moiety, NH—CO or CO—NH; a 1,4-phenylene; or a 1,4-phenylenemethylene moiety, said moiety being optionally substituted by at least one linear or branched alkyl or alkoxy group and/or halogen atom; and wherein $R_D$ is a linear or branched acyclic, cyclic or multicyclic moiety, said moiety being optionally unsaturated and/or substituted by at least one hydrogen, $OR^i$, amino, alkyl- or dialkylamino, $NHCOR^i$, halogen, $CH_2OH$, $CH_2OR^i$, a substituted or unsubstituted linear or branched chain alkyl, (mono-, di- or tri) hydroxyalkyl, (mono-, di- or tri)acyloxyalkyl, arylalkyl or aryl group; wherein $R^i$ is hydrogen, CHO, $COOR^{ii}$, or a substituted or unsubstituted linear or branched chain alkyl, arylalkyl or aryl group aryl, alkylaryl or arylalkyl; wherein $R^{ii}$ is hydrogen, a substituted or unsubstituted linear or branched chain alkyl, arylalkyl, or aryl group; wherein if $R_D$ is cyclic, said moiety is optionally aromatic and/or heterocyclic; or if multicyclic, said moiety is optionally a fused multicyclic, fully or partially aromatic and/or heterocyclic.

6. The method of claim 5, further comprising the step of treating said modified polymer-linked composition with a cleaving agent under suitable conditions to generate an alcohol having the structure $R_D$—OH and a reusable polymeric alcohol support.

7. The method of claim 3 or 5, wherein the cleaving agent is a fluoride reagent, a strong acid, or a strong nucleophile.

8. The method of claim 7 wherein the fluoride reagent is tetraalkylammonium fluoride, tetra-n-butylammonium fluoride or pyridinium fluoride.

9. The method of claim 7, wherein the cleaving agent is NaOH, MeLi, acetic acid, methanesulfonic acid, trifluoroacetic acid, or trifluoromethanesulfonic acid.

10. The method of claim 5 wherein $R_D$ is a carbohydrate having the structure:

wherein a, b, c, d, e and f are each independently 0, 1, 2 or 3 with the proviso that $R_D$ is a furanose or pyranose moiety and the sum of a, b, d and e is 1 or 2; wherein $R_1$, $R_2$, $R_3$, $R_4$, $R_5$ and $R_6$ are independently hydrogen, OH, $OR^i$, amino, $NHCOR^i$, halogen, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein $R^i$ is hydrogen, CHO, $COOR^{ii}$, or a substituted or unsubstituted linear or branched chain alkyl, arylalkyl or aryl group; wherein $R^{ii}$ is hydrogen, a substituted or unsubstituted linear or branched chain alkyl, arylalkyl or aryl group; and wherein the dotted line represents an optional double bond; wherein when said double bond is present, $R_1$ and $R_2$ are not both OH or amino.

11. The method of claim 5, wherein the polymer-linked composition is subjected to one or more glycosylation reactions to generate a modified polymer-linked composition, wherein $R_D$ is a complex carbohydrate having the structure:

wherein a, b, c, d, e, f, g, h, i, j, k, q, n, p, x and y are each independently 1, 2 or 3, with the proviso that $R_D$ is a carbohydrate having furanose of pyranose moieties whereby the sum of b and c is 1 or 2, the sum of d and f is 1 or 2, the sum of g and i is 1 or 2, and the sum of n, p, k and j is 2 or 3; wherein $R_0$, $R_1$, $R_2$, $R_3$, $R_4$, $R_5$, $R_6$, $R_7$, $R_8$, $R_9$, $R_{10}$, $R_{11}$, $R_{12}$, and $R_{13}$ are each independently hydrogen, OH, $OR^i$, $NH_2$, $NHCOR^i$, F, $CH_2OH$, $CH_2OR^i$, a protecting group, a substituted or unsubstituted linear or branched chain alkyl, (mono-, di- or tri)hydroxyalkyl, (mono-, di- or tri)acyloxyalkyl, arylalkyl or aryl group; wherein $R^i$ is hydrogen, CHO, $COOR^{ii}$, a substituted or unsubstituted linear or branched chain alkyl, arylalkyl or aryl group or a saccharide moiety having the structure:

wherein Y and Z are each independently NH or O; wherein r, s, t, u, v, w, z and z' are each independently 0, 1 or 2, with the proviso that z and z' bracketed structures represent furanose or pyranose moieties and the sum of s and t is 1 or 2, and the sum of u and w is 1 or 2, and with the proviso that z and z' are not simultaneously 0; wherein $R_x$ is hydrogen, a linear or branched chain alkyl, acyl, arylalkyl or aryl group; wherein $R_{14}$, $R_{15}$, $R_{17}$, $R_{18}$, $R_{19}$, and $R_{20}$ are each independently hydrogen, OH, $OR^{iii}$, $NH_2$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri) acyloxyalkyl, arylalkyl or aryl group; wherein $R_{16}$ is hydrogen, COOH, $COOR^{ii}$, $CONHR^{ii}$, a substituted or unsubstituted linear or branched chain alkyl or aryl group; wherein $R^{iii}$ is hydrogen, CHO, $COOR^{iv}$, or a substituted or unsubstituted linear or branched chain alkyl, arylalkyl or aryl group; and wherein $R^{ii}$ and $R^{iv}$ are each independently H, or a substituted or unsubstituted linear or branched chain alkyl, arylalkyl or aryl group, or wherein any two of $R_0$–$R_{13}$, taken together, comprise a cyclic protecting group; wherein the dotted line represents an optional double bond; wherein when said double bond is present, $R_0$ and $R_3$ are not both OH or amino; and wherein said carbohydrate is optionally linked to an amino acyl or hydroxy acyl residue of a substructure by substitution of a side group or terminal group substituent thereof selected from the group consisting of OH, COOH and $NH_2$, said substructure being:

wherein m, n, p and q are 0, 1, 2 or 3 such that m+n+p+q≦6; wherein A, B, C, D, E and F are independently amino acyl or hydroxy acyl residues wherein A is N- or O-terminal and is either a free amine or an ammonium form when A is amino acyl or a free hydroxy when A is hydroxy acyl, or A is alkylated, arylated or acylated; and wherein F is either a free carboxylic acid, primary carboxamide, mono- or dialkyl carboxamide, mono- or diaryl-carboxamide, linear or branched chain (carboxy)alkyl carboxamide, linear or branched chain (alkoxycarbonyl)alkyl-carboxamide, linear or branched chain (carboxy)arylalkylcarboxamide, linear or branched chain (alkoxycarbonyl)-alkylcarboxamide, an oligoester fragment comprising from 2 to about 20 hydroxy acyl residues, a peptidic fragment comprising from 2 to about 20 amino acyl residues, or a linear or branched chain alkyl or aryl carboxylic ester.

12. The method of claim 11, further comprising a step of treating said modified polymer-linked composition with a cleaving agent under suitable conditions to generate an alcohol $R_D$—OH and a reusable polymeric alcohol.

13. The method of claim 1, wherein the base is imidazole.

14. The method of claim 1, wherein the base is selected from the group consisting of pyridine, DBU, diisopropylethylamine, triethylamine, and dimethyl aminopyridine.

15. The method of claim 1 wherein $R_C$ is a carbohydrate having the structure:

wherein a, b, c, d, e, f, g, h, i, j, k, q, n, p, x and y are each independently 1, 2 or 3, with the proviso that $R_C$ is a carbohydrate having furanose of pyranose moieties whereby the sum of b and c is 1 or 2, the sum of d and f is 1 or 2, the sum of and i is 1 or 2, and the sum of n, p, k and j is 2 or 3; wherein $R_0$, $R_1$, $R_2$, $R_3$, $R_4$, $R_5$, $R_6$, $R_7$, $R_8$, $R_9$, $R_{10}$, $R_{11}$, and $R_{12}$, and $R_{13}$, are each independently hydrogen, OH, $OR^i$, $NH_2$, $NHCOR^i$, F, $CH_2OH$, $CH_2OR^i$, a protecting group, a substituted or unsubstituted linear or branched chain alkyl, (mono-, di- or tri)hydroxyalkyl, (mono-, di- or tri)acyloxyalkyl, arylalkyl or aryl group; wherein $R^i$ is hydrogen, CHO, $COOR^{ii}$, a substituted or unsubstituted linear or branched chain alkyl, arylalkyl or aryl group or a saccharide moiety having the structure:

wherein Y and Z are each independently NH or O; wherein r, s, t, u, v, w, z and z' are each independently 0, 1 or 2, with the proviso that z and z' bracketed structures represent furanose or pyranose moieties and the sum of s and t is 1 or 2, and the sum of u and w is 1 or 2, and with the proviso that z and z' are not simultaneously 0; wherein $R_x$ is hydrogen, a linear or branched chain alkyl, acyl, arylalkyl or aryl group; wherein $R_{14}$, $R_{15}$, $R_{17}$, $R_{18}$, $R_{19}$, and $R_{20}$ are each independently hydrogen, OH, $OR^{iii}$, $NH_2$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri) acyloxyalkyl, arylalkyl or aryl group; wherein $R_{16}$ is hydrogen, COOH, $COOR^{ii}$, $CONHR^{ii}$, a substituted or unsubstituted linear or branched chain alkyl or aryl group; wherein $R^{iii}$ is hydrogen, CHO, $COOR^{iv}$, or a substituted or unsubstituted linear or branched chain alkyl, arylalkyl or aryl group; and wherein $R^{ii}$ and $R^{iv}$ are each independently H, or a substituted or unsubstituted linear or branched chain alkyl, arylalkyl or aryl group, or wherein any two of $R_0$–$R_{13}$, taken together, comprise a cyclic protecting group; wherein the dotted line represents an optional double bond; wherein when said double bond is present, $R_0$ and $R_3$ are not both OH or amino; and wherein said carbohydrate is optionally linked to an amino acyl or hydroxy acyl residue of a substructure by substitution of a side group or terminal group substituent thereof selected from the group consisting of OH, COOH and $NH_2$, said substructure being:

wherein m, n, p and q are 0, 1, 2 or 3 such that m+n+p+q≦6; wherein A, B, C, D, E and F are independently amino acyl or hydroxy acyl residues wherein A is N- or O-terminal and is either a free amine or an ammonium form when A is amino acyl or a free hydroxy when A is hydroxy acyl, or A is alkylated, arylated or acylated; and wherein F is either a free carboxylic acid, primary carboxamide, mono- or dialkyl carboxamide, mono- or diaryl-carboxamide, linear or branched chain (carboxy)alkyl carboxamide, linear or branched chain (alkoxycarbonyl)alkyl-carboxamide, linear or branched chain (carboxy) arylalkylcarboxamide, linear or branched chain (alkoxycarbonyl)-alkylcarboxamide, an oligoester fragment comprising from 2 to about 20 hydroxy acyl residues, a peptidic fragment comprising from 2 to about 20 amino acyl residues, or a linear or branched chain alkyl or aryl carboxylic ester.

16. The method of claim 1 wherein $R_C$ is a carbohydrate having the structure:

wherein a, b, c, d, e and f are each independently 0, 1, 2 or 3 with the proviso that $R_C$ is a furanose or pyranose moiety and the sum of a, b, d and e is 1 or 2; wherein $R_1$, $R_2$, $R_3$, $R_4$, $R_5$, and $R_6$ are independently hydrogen, OH, OR$^i$, amino, NHCOR$^i$, halogen, CH$_2$OH, CH$_2$OR$^i$, a substituted or unsubstituted linear or branched chain alkyl, (mono-, di- or tri)hydroxyalkyl, (mono-, di- or tri)acyloxyalkyl, arylalkyl or aryl group; wherein R$^i$ is hydrogen, CHO, COOR$^{ii}$, or a substituted or unsubstituted linear or branched chain alkyl, arylalkyl or aryl group; wherein R$^{ii}$ is hydrogen, a substituted or unsubstituted linear or branched chain alkyl, arylalkyl or aryl group; and wherein the dotted line represents an optional double bond; wherein when said double bond is present, $R_1$ and $R_2$ are not both OH or amino.

17. The method of claim 1 wherein $R_A$ and $R_B$ are each isopropyl.

18. The method of claim 1 wherein L is 1,4-phenylenemethylene, and the composition has the structure:

19. The method of claim 1, wherein $R_C$ is a carbohydrate having the structure:

wherein $R_3$, $R_4$, $R_5$ and $R_6$, are, for each occurrence, independently hydrogen, OH, OR$^i$, amino, NHCOR$^i$, halogen, CH$_2$OH, CH$_2$OR$^i$, a substituted or unsubstituted linear or branched chain alkyl, (mono-, di- or tri)hydroxyalkyl, (mono-, di- or tri)acyloxyalkyl, arylalkyl or aryl group; wherein R$^i$ is hydrogen, CHO, COOR$^{ii}$, or a substituted or unsubstituted linear or branched chain alkyl, arylalkyl or aryl group; wherein R$^{ii}$ is hydrogen, a substituted or unsubstituted linear or branched chain alkyl, arylalkyl or aryl group; and wherein f is 0, 1, 2 or 3.

20. The method of claim 1 wherein $R_C$ is a carbohydrate having the structure:

wherein $R_3$, $R_4$, $R_5$ and $R_6$, are, for each occurrence, independently hydrogen, OH, OR$^i$, amino, NHCOR$^i$, halogen, CH$_2$OH, CH$_2$OR$^i$, a substituted or unsubstituted linear or branched chain alkyl, (mono-, di- or tri)hydroxyalkyl, (mono-, di- or tri)acyloxyalkyl, arylalkyl or aryl group; wherein R$^i$ is hydrogen, CHO, COOR$^{ii}$, or a substituted or unsubstituted linear or branched chain alkyl, arylalkyl or aryl group; wherein R$^{ii}$ is hydrogen, a substituted or unsubstituted linear or branched chain alkyl, arylalkyl or aryl group; and wherein f is 0, 1, 2 or 3.

21. The method of claim 1 wherein the polymeric alcohol support is selected from the group consisting of poly((p-hydroxymethylphenyl)ethylene), poly((p hydroxyphenyl)ethylene) and poly((hydroxymethyl)ethylene).

22. The method of claim 21 wherein the polymeric alcohol support is in resin bead form.

23. The method of claim 1 wherein X is chlorine.

24. A method for the modification of alcohols on polymer supports comprising:
   (a) O-silylating an alcohol, $R_C$—OH, with $X_2SiR_AR_B$, wherein X is a halogen, and $R_A$ and $R_B$ are each independently a $C_{1-6}$ linear or $C_{3-10}$ branched chain alkyl or an aryl group, in the presence of base under conditions to form a halosilyl compound; and
   (b) coupling said halosilyl compound with a polymeric alcohol support in the presence of base under conditions to form a polymer-linked composition having the following structure:

wherein $R_A$ and $R_B$ are each independently a $C_{1-6}$ linear or $C_{3-10}$ branched chain alkyl or an aryl group;

wherein Ⓟ is a polymeric support;

wherein L is a linker selected from the group consisting of a single bond; a saturated or unsaturated oligomethylene chain, said oligomethylene chain being optionally interrupted by oxygen or sulfur atoms, an alkyl- or arylamino moiety, NH—CO or CO—NH; a 1,4-phenylene; or a 1,4-phenylenemethylene moiety, said moiety being optionally substituted by at least one linear or branched alkyl or alkoxy group and/or halogen atom; and wherein $R_C$ is a linear or branched acyclic, cyclic or multicyclic moiety, said moiety being optionally unsaturated and/or substituted by at least one hydrogen, OR$^i$, amino, alkyl- or dialkylamino, NHCOR$^i$, halogen, CH$_2$OH, CH$_2$OR$^i$, a substituted or unsubstituted linear or branched chain alkyl, (mono-, di- or tri)hydroxyalkyl, (mono-, di- or tri)acyloxyalkyl, arylalkyl or aryl group; wherein R$^i$ is hydrogen, CHO, COOR$^{ii}$, or a substituted or unsubstituted linear or branched chain alkyl, arylalkyl or aryl group aryl, alkylaryl or arylalkyl; wherein if $R_C$ is cyclic, said moiety is optionally aromatic and/or heterocyclic; or if multicyclic, said moiety is optionally a fused multicyclic, fully or partially aromatic and/or heterocyclic; and (c) subjecting said polymer-linked composition to one or more chemical reactions to generate a support-bound complex carbohydrate as the modified polymer-linked composition, which composition has the following structure:

wherein $R_A$ and $R_B$ are each independently a $C_{1-6}$ linear or $C_{3-10}$ branched chain alkyl or an aryl group;

wherein ⓟ is a polymeric support;

wherein L is a linker selected from the group consisting of a single bond; a saturated or unsaturated oligomethylene chain, said oligomethylene chain being optionally interrupted by oxygen or sulfur atoms, an alkyl- or arylamino moiety, NH—CO or CO—NH; a 1,4-phenylene; or a 1,4-phenylenemethylene moiety, said moiety being optionally substituted by at least one linear or branched alkyl or alkoxy group and/or halogen atom; and wherein $R_D$ is:

wherein a, b, c, d, e, f, g, h, i, j, k, q, n, p, x and y are each independently 1, 2 or 3, with the proviso that $R_D$ is a carbohydrate having furanose or pyranose moieties whereby the sum of b and c is 1 or 2, the sum of d and f is 1 or 2, the sum of g and i is 1 or 2, and the sum of n, p, k and j is 2 or 3; wherein $R_0$, $R_1$, $R_2$, $R_3$, $R_4$, $R_5$, $R_6$, $R_7$, $R_8$, $R_9$, $R_{10}$, $R_{11}$, $R_{12}$, and $R_{13}$ are each independently hydrogen, OH, $OR^i$, $NH_2$, $NHCOR^i$, F, $CH_2OH$, $CH_2OR^i$, a protecting group, a substituted or unsubstituted linear or branched chain alkyl, (mono-, di- or tri)hydroxyalkyl, (mono-, di- or tri)acyloxyalkyl, arylalkyl or aryl group; wherein $R^i$ is hydrogen, CHO, $COOR^{ii}$, a substituted or unsubstituted linear or branched chain alkyl, arylalkyl or aryl group or a saccharide moiety having the structure:

wherein Y and Z are each independently NH or O; wherein r, s, t, u, v, w, z and z' are each independently 0, 1 or 2, with the proviso that z and z' bracketed structures represent furanose or pyranose moieties and the sum of s and t is 1 or 2, and the sum of u and w is 1 or 2, and with the proviso that z and z' are not simultaneously 0; wherein $R_x$ is hydrogen, a linear or branched chain alkyl, acyl, arylalkyl or aryl group; wherein $R_{14}$, $R_{15}$, $R_{17}$, $R_{18}$, $R_{19}$, and $R_{20}$ are each independently hydrogen, OH, $OR^{iii}$, $NH_2$, $NHCOR^{iii}$, F, $CH_2OH$, $CH_2OR^{iii}$, or a substituted or unsubstituted linear or branched chain alkyl, (mono-, di- or tri) hydroxyalkyl, (mono-, di- or tri)acyloxyalkyl, arylalkyl or aryl group; wherein $R_{16}$ is hydrogen, COOH, $COOR^{ii}$, $CONHR^{ii}$, a substituted or unsubstituted linear or branched chain alkyl or aryl group; wherein $R^{iii}$ is hydrogen, CHO, $COOR^{iv}$, or a substituted or unsubstituted linear or branched chain alkyl, arylalkyl or aryl group; and wherein $R^{ii}$ and $R^{iv}$ are each independently H, or a substituted or unsubstituted linear or branched chain alkyl, arylalkyl or aryl group, or wherein any two of $R_0$–$R_{13}$, taken together, comprise a cyclic protecting group;

wherein the dotted line represents an optional double bond; wherein when said double bond is present, $R_0$ and $R_3$ are not both OH or amino; and wherein said carbohydrate is optionally linked to an amino acyl or hydroxy acyl residue of a substructure by substitution of a side group or terminal group substituent thereof selected from the group consisting of OH, COOH and $NH_2$, said substructure being:

wherein m, n, p and q are 0, 1, 2 or 3 such that $m+n+p+q \leq 6$; wherein A, B, C, D, E and F are independently amino acyl or hydroxy acyl residues wherein A is N- or O-terminal and is either a free amine or an ammonium form when A is amino acyl or a free hydroxy when A is hydroxy acyl, or A is alkylated, arylated or acylated; and wherein F is either a free carboxylic acid, primary carboxamide, mono- or dialkyl carboxamide, mono- or diarylcarboxamide, linear or branched chain (carboxy)alkyl carboxamide, linear or branched chain (alkoxycarbonyl)alkylcarboxamide, linear or branched chain (carboxy)arylalkylcarboxamide, linear or branched chain (alkoxycarbonyl)-alkylcarboxamide, an oligoester fragment comprising from 2 to about 20 hydroxy acyl residues, a peptidic fragment comprising from 2 to about 20 amino acyl residues, or a linear or branched chain alkyl or aryl carboxylic ester; and

(d) treating said modified polymer-linked composition with a cleaving agent under suitable conditions to generate an alcohol, $R_D$—OH, and a reusable polymeric alcohol support.

25. The method of claim 24, further comprising the step of reusing said polymeric alcohol support, which step comprises:

O-silylating an alcohol $R_C$—OH, with $X_2SiR_AR_B$, wherein X is a halogen, and $R_A$ and $R_B$ are each independently a $C_{1-6}$ linear or $C_{3-10}$ branched chain alkyl or an aryl group, in the presence of a base under conditions to form a halosilyl compound; and coupling said halosilyl compound with a polymeric alcohol support in the presence of a base under conditions to form a polymer-linked composition having the structure:

wherein $R_A$ and $R_B$ are each independently a $C_{1-6}$ linear or $C_{3-10}$ branched chain alkyl or an aryl group;

wherein  is a polymeric support;

wherein L is a linker selected from the group consisting of a single bond; a saturated or unsaturated oligomethylene chain, said oligomethylene chain being optionally interrupted by oxygen or sulfur atoms, an alkyl- or arylamino moiety, NH—CO or CO—NH, a 1,4-phenylene; or a 1,4-phenylenemethylene moiety, said moiety being optionally substituted by at least one linear or branched alkyl or alkoxy group and/or halogen atom, whereby said polymer-linked composition comprises at least one reactive moiety so that the polymer-linked composition can be subjected to one or more chemical reactions to generate a modified polymer-linked composition.

26. The method of claim 24, wherein $R_D$ is:

wherein P comprises a peptidic fragment comprising from 2 to about 20 amino acyl residues.

27. The method of claim 26, wherein said peptidic fragment comprises:

```
CbzAlaLeuAspLeuThr—COOAll
        |
        OBn
```

* * * * *